US012569258B1

(12) United States Patent
Abboud

(10) Patent No.: US 12,569,258 B1
(45) Date of Patent: Mar. 10, 2026

(54) DRILL BIT-HAVING BONE CONDENSATION TECHNIQUE

(71) Applicant: Marcus Abboud, Avon, CO (US)

(72) Inventor: Marcus Abboud, Avon, CO (US)

(73) Assignee: Venetian Trust, Avon, CO (US)

( * ) Notice: Subject to any disclaimer, the term of this patent is extended or adjusted under 35 U.S.C. 154(b) by 0 days.

(21) Appl. No.: 19/312,237

(22) Filed: Aug. 27, 2025

(51) Int. Cl.
*A61B 17/16* (2006.01)

(52) U.S. Cl.
CPC ................................. *A61B 17/1615* (2013.01)

(58) Field of Classification Search
CPC . A61B 17/1615; A61B 17/885; A61C 8/0089;
A61C 8/009; A61C 8/0092; B23B
2251/406; B23B 2251/4062
See application file for complete search history.

(56) References Cited

U.S. PATENT DOCUMENTS

| | | | | |
|---|---|---|---|---|
| 3,598,500 A | * | 8/1971 | Oxford, Jr. ............. | B23B 51/02 |
| | | | | 408/230 |
| 4,944,640 A | * | 7/1990 | Suzuki .................... | B23B 51/00 |
| | | | | 408/229 |
| 5,071,294 A | * | 12/1991 | Suzuki .................... | B23B 51/00 |
| | | | | 408/145 |
| 5,143,490 A | * | 9/1992 | Kopras .................... | B23C 5/10 |
| | | | | 407/54 |
| 5,486,075 A | * | 1/1996 | Nakamura .............. | B23B 51/02 |
| | | | | 408/230 |

| | | | | |
|---|---|---|---|---|
| 5,685,673 A | * | 11/1997 | Jarvis ..................... | B23Q 11/10 |
| | | | | 408/230 |
| 10,039,621 B2 | * | 8/2018 | Huwais ................ | A61C 8/0089 |
| 2003/0175086 A1 | * | 9/2003 | Muhlfriedel ............ | B24B 19/04 |
| | | | | 408/230 |
| 2011/0207081 A1 | * | 8/2011 | Jensen ..................... | A61C 5/40 |
| | | | | 433/224 |
| 2013/0004918 A1 | * | 1/2013 | Huwais .............. | A61B 17/1615 |
| | | | | 433/173 |
| 2013/0006248 A1 | * | 1/2013 | Ellis ................... | A61B 17/1615 |
| | | | | 451/48 |
| 2013/0189044 A1 | * | 7/2013 | Durfee ................... | B23B 51/02 |
| | | | | 408/214 |
| 2013/0253521 A1 | * | 9/2013 | Ellis ................... | A61B 17/1655 |
| | | | | 606/80 |
| 2015/0283625 A1 | * | 10/2015 | Sato ........................ | B23B 51/02 |
| | | | | 408/230 |
| 2018/0071836 A1 | * | 3/2018 | Fukushima ............. | B23B 51/02 |
| 2018/0250755 A1 | * | 9/2018 | George .................. | B23B 51/02 |

(Continued)

*Primary Examiner* — Andrew Yang
(74) *Attorney, Agent, or Firm* — CM Law LLP; Robert C. Klinger

(57) ABSTRACT

A drill bit configured to simultaneously direct debris toward a drill bit tip and compress the debris into a sidewall of a hole during rotation in a single direction to strengthen the hole to receive an implant. The drill bit may comprise an osteotome, the hole may comprise an osteotomy, and the implant may be a dental implant. In an example, due to the right-hand (clockwise) rotation of the drill bit, a helical flute exhibits an apparent counterclockwise movement relative to a stationary observer, commonly referred to as apparent flute motion. The drill bit is configured to simultaneously direct the created debris longitudinally toward the tip while the first land area compresses the debris laterally outward from the drill bit into a side wall of a drill hole during rotation of the drill bit in a single direction.

20 Claims, 4 Drawing Sheets

(56)     References Cited

U.S. PATENT DOCUMENTS

2021/0290346 A1*  9/2021  Huwais .............. A61B 17/1615
2025/0186063 A1*  6/2025  Huwais .............. A61B 17/1673
2025/0228570 A1*  7/2025  Suh ................... A61B 17/1615

* cited by examiner

200

114
106
108
112   202
110

700

702 — Secure drill bit to drill

704 — Rotate drill bit

706 — Create debris and compress the debris during a single process

708 — Secure implant to drill hole

DRILL BIT-HAVING BONE CONDENSATION TECHNIQUE

TECHNICAL FIELD

The present disclosure relates to drill bits, including but not limited to bits for bone drilling purposes such as an osteotome.

BACKGROUND

Drill bits cut through material and generate debris, such as bone chips. To perform an osteotomy, a drill bit is typically rotated in two directions.

DETAILED DESCRIPTION

Figure 1:
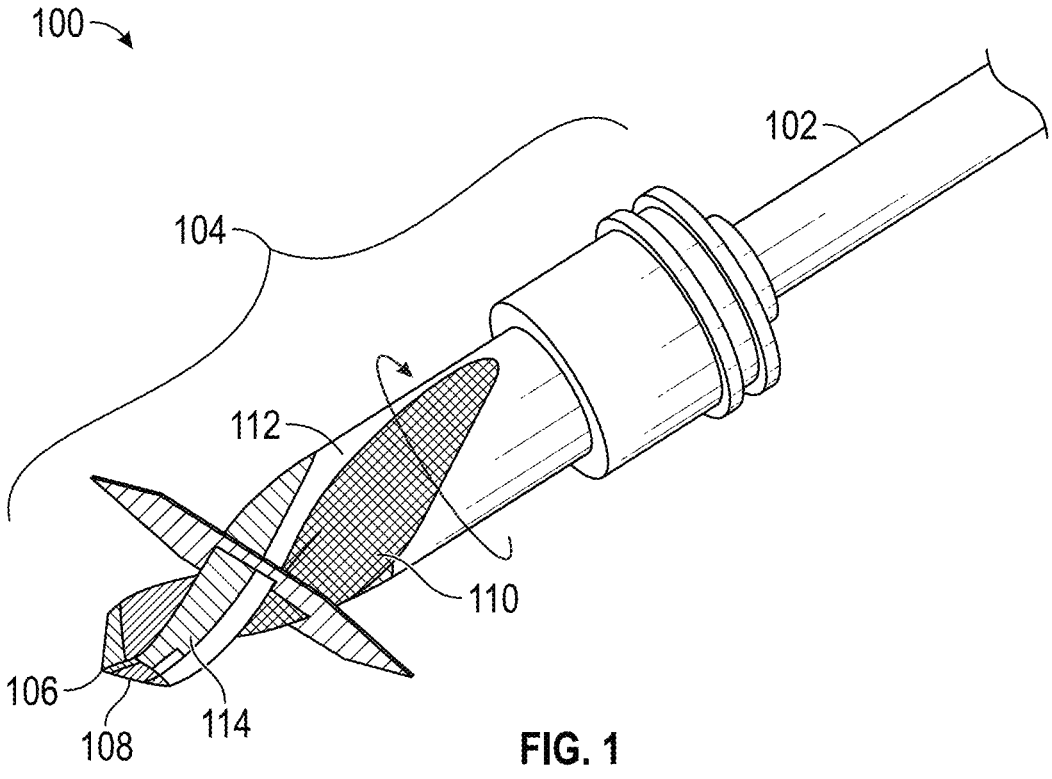
FIG. 1 is a perspective view of a drill bit.

This disclosure includes a drill bit configured to simultaneously create debris and direct the debris toward the drill bit tip and compress the debris into a sidewall of a hole during rotation in a single direction to strengthen the hole to receive an implant. The drill bit may comprise an osteotome, the hole may comprise an osteotomy, and the implant may be a dental implant. In an example, due to the right-hand (clockwise) rotation of the drill bit, a helical flute exhibits an apparent counterclockwise movement relative to a stationary observer, commonly referred to as apparent flute motion. The drill bit is configured to simultaneously direct the created debris longitudinally toward the tip while the first land area compresses the debris laterally outward from the drill bit into a side wall of a drill hole during rotation of the drill bit in a single direction.

Additional objects, advantages and novel features of the examples will be set forth in part in the description which follows, and in part will become apparent to those skilled in the art upon examination of the following and the accompanying drawings or may be learned by production or operation of the examples. The objects and advantages of the present subject matter may be realized and attained by means of the methodologies, instrumentalities and combinations particularly pointed out in the appended claims.

In the following detailed description, numerous specific details are set forth by way of examples in order to provide a thorough understanding of the relevant teachings. However, it should be apparent to those skilled in the art that the present teachings may be practiced without such details. In other instances, well-known methods, procedures, components, and circuitry have been described at a relatively high-level, without detail, in order to avoid unnecessarily obscuring aspects of the present teachings.

The term "coupled" as used herein refers to any logical, optical, physical or electrical connection, link or the like by which signals, or light produced or supplied by one system element are imparted to another coupled element. Unless described otherwise, coupled elements or devices are not necessarily directly connected to one another and may be separated by intermediate components, elements or communication media that may modify, manipulate or carry the light, sound, or signals.

Bone condensation is a widely used technique for improving implant stability, particularly in low-density bone, such as mammalian bone. Bone quality is classified into four categories, D1 through D4, with D1 being the hardest and D4 the lowest density. D4 bone almost always requires condensation, while D3 bone occasionally benefits from additional stability enhancements.

To achieve bone condensation, this disclosure includes a drill bit, referred to as an osteotome, having a unique drill bit design that presses the removed bone debris into the surrounding material of an osteotomy during the drilling process by burnishing, creating a denser structure to support the implant.

Referring to FIG. 1 there is shown a perspective view of a longitudinally extending drill bit 100 having a shank 102 at a proximal end and a body 104 extending from the shank 102 to a distal end including a cutting tip 106. Tip 106 includes a lip relief 108. The body 104 includes a helical shaped (helix) flute 110 and a land area 112 that represents a guiding phase. This land area 112 is positioned above a land area 114 at the top of the land area 114, not below it, where land area 112 is the widest diameter of the drill bit body 104. Land area 114 tapers inwardly from land area 112 and controls the flow of debris toward the land area 112. The width of land area 112 is narrower than a width of land area 114. Land area 114 is formed on a side of land area 112 opposite the helical flute 110. Land area 112 has less surface area than an area of helical flute 110. As the drill bit 100 rotates right into a material surface such as bone during an osteotomy, shown in FIG. 1 as a clockwise direction when viewed from the shank 102 and looking down the axis of the drill bit 100, the drill bit 100 counteracts a rightward rotation of the drill itself, but the helical flute s 110 spirals counterclockwise to direct debris toward the tip 106 to compress debris. This is referred to as a reverse-spiral flute drill bit.

The helical flute 110 directs debris, such as bone chips, created by cutting tip 106 and lip relief 108 longitudinally toward tip 106 of the drill bit 100 and also channels the debris through the land area 114, referred to as a chip channel, and the land area 112 ultimately presses the debris laterally into the surrounding bone ensuring the bone is effectively compacted into the surrounding bone material. This single process of rotating drill bit 100 in a single direction both drills bone and also compresses the bone debris during an osteotomy to create a denser structure to support an implant, such a dental implant, knee implant, or other bone implant. It is noted that the design of drill bit 100 and all features can be configured to be rotated where the single direction is in the counterclockwise direction.

Figure 2:
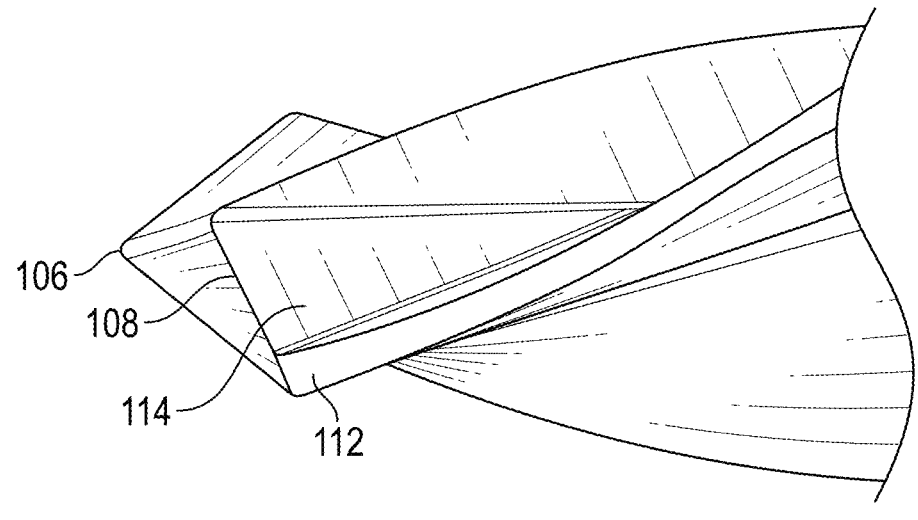
FIG. 2 is an enlarged perspective view of the drill bit illustrating a land area configured to direct debris towards the drill bit tip.

FIG. 2 is an enlarged perspective view of drill bit 100 illustrating land area 114 configured to direct debris toward tip 106. As the debris accumulates in the land area 114, land area 112 presses the debris toward the side walls of a drill hole to compress the debris into the side walls, creating a denser side wall during the burnishing process.

Figures 3, 4:
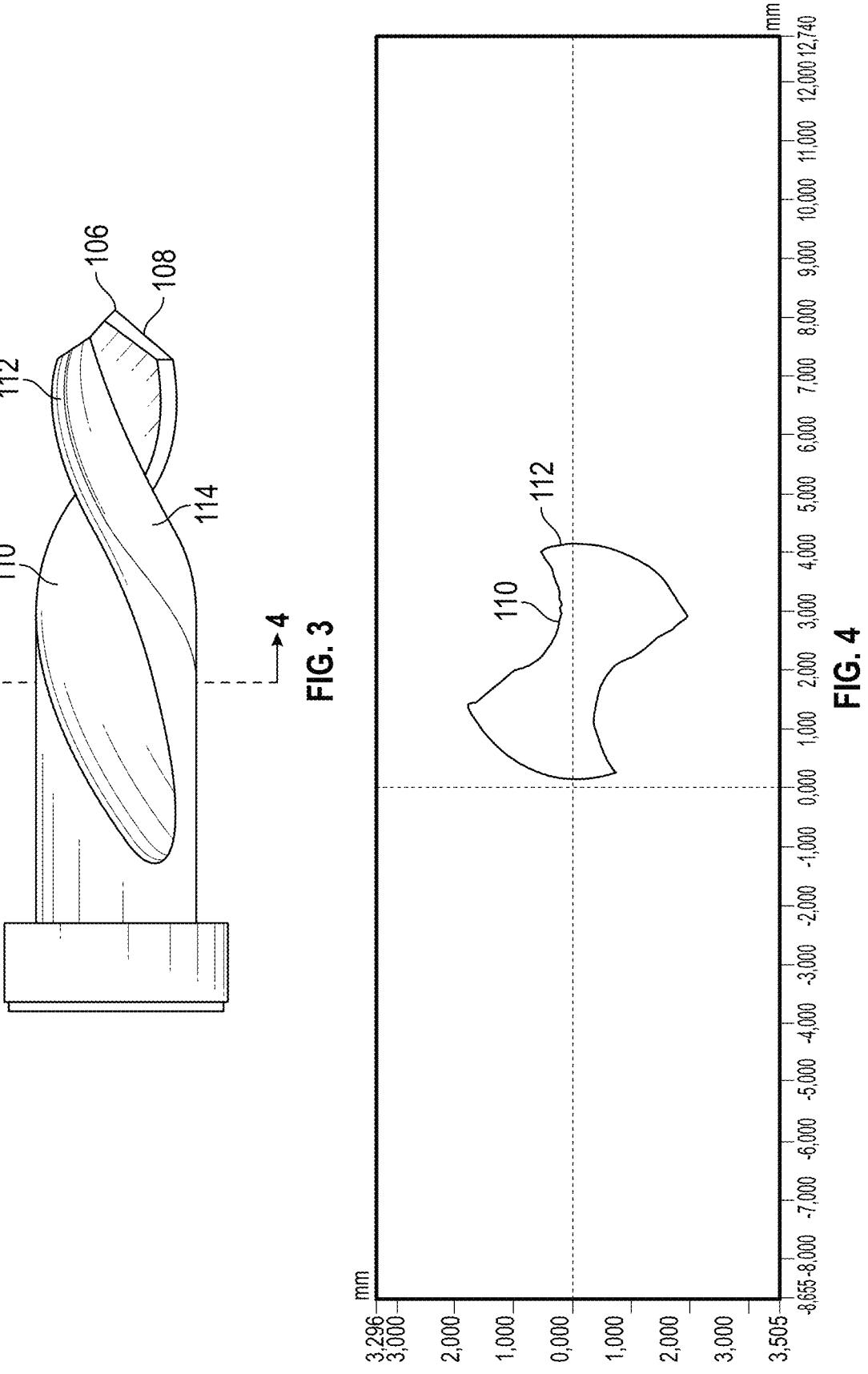
FIG. 3 illustrates a side view of the drill bit.
FIG. 4 illustrates a cross-sectional view of the drill bit taken along line 4-4 in FIG. 3.

FIG. 3 illustrates a side view of drill bit 100.

FIG. 4 illustrates a cross-sectional view of drill bit 100 taken along line 4-4 in FIG. 3;

US 12,569,258 B1

3

Figure 5:
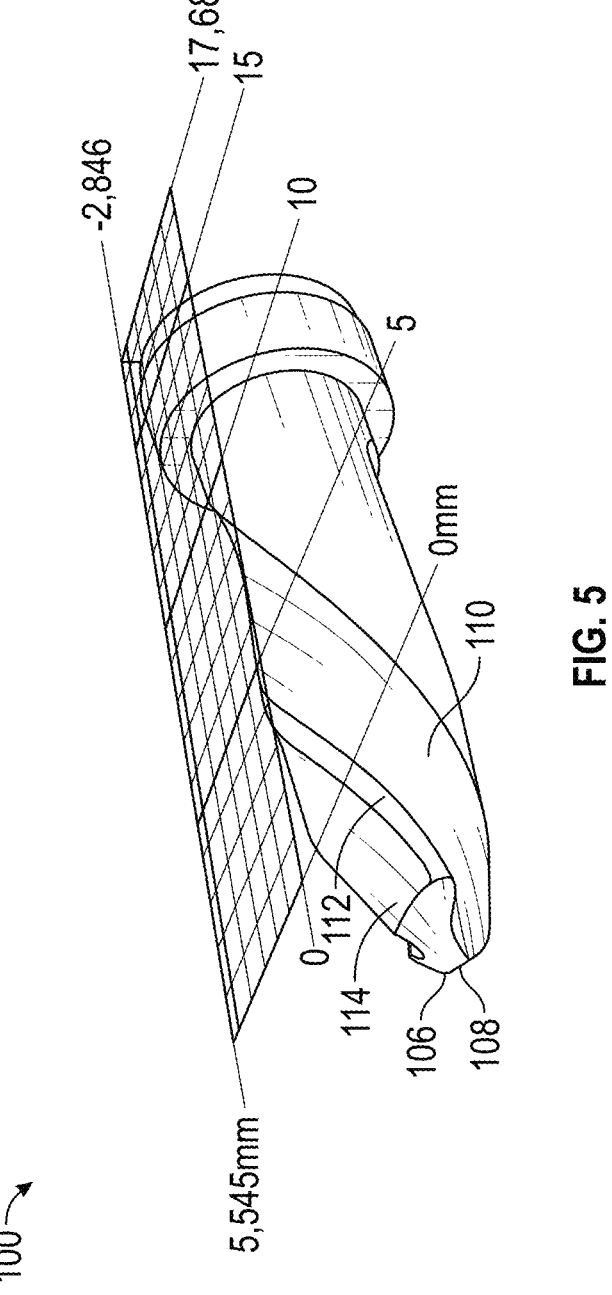
FIG. 5 illustrates example dimensions of the drill bit.

FIG. 5 illustrates example dimensions of drill bit 100 in one exemplary embodiment. Other dimensions are suitable and limitation to these specific dimensions is not to be inferred.

Figure 6:
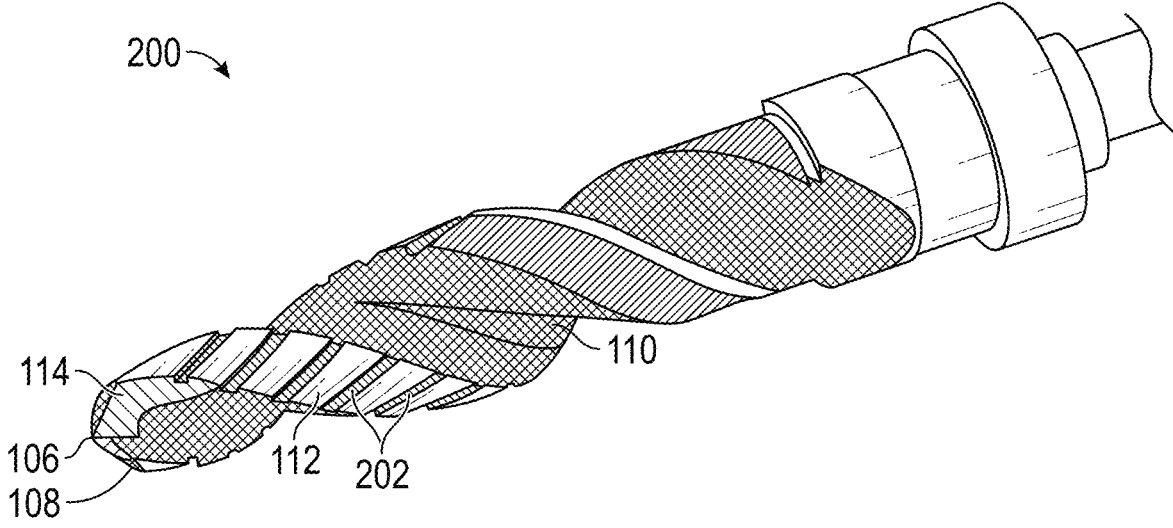
FIG. 6 illustrates a drill bit according to another embodiment of the disclosure.

FIG. 6 illustrates a drill bit 200 according to another embodiment of the disclosure that is similar to drill bit 100, wherein like numerals refer to like elements. Drill bit 200 includes longitudinal channels 202 extending across land area 112 that further enhance the bone condensation process, ensuring the bone debris is effectively compacted into the surrounding material. Channels 202 hold bone debris such that the bone debris is compressed against the side walls of the drill hole during the burnishing process. In other words, bone debris occludes channels 202 to create more friction and lateral pressure of the bone debris against the side walls.

Figure 7:
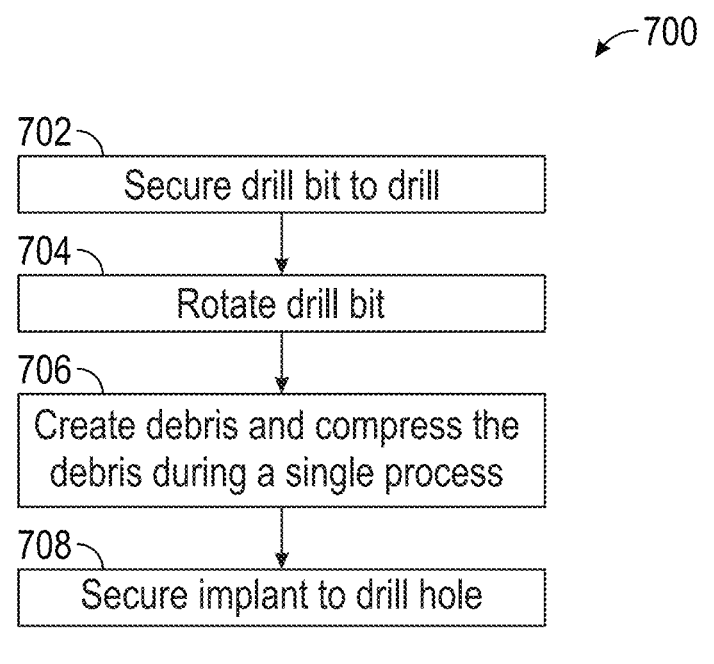
FIG. 7 is a block diagram of a method of using the drill bit to drill into a material.

FIG. 7 is a block diagram of method 700 performing an osteotomy using the drill bits 100 and 200.

At step 702, a selected drill bit 100 or 200 is secured to a drill (not shown). The drill can be any common drill typically used during an osteotomy.

At step 704, the drill rotates the selected drill bit 100 or 200 in a direction, such as a clockwise direction as shown in FIG. 1 in an osteotomy such that drill tip 100 and lip relief 108 are pressed into a drill hole to enlarge the hole and create bone debris.

At step 706, the generated bone debris is channeled by land area 114 toward the drill tip 106, such that the debris is compressed by land area 112 into the side wall of the drill hole to condense the bone and strengthen the bone and create additional stability for an implant. The rotation of the drill bit 100 and 200 both opens the hole and compresses the debris into the drill hole side walls during a single process. In this example, due to the right-hand (clockwise) rotation of the drill bit 100, the helical flute 110 exhibits an apparent counterclockwise movement relative to a stationary observer creating apparent flute motion. The drill bit is configured to simultaneously direct the created debris toward the tip in the longitudinal direction while the first land area compresses the debris laterally outward from the drill bit into a side wall of a drill hole during rotation of the drill bit in a single direction.

At step 708, an implant can be secured to the drill hole. The implant can be a dental implant, knee implant, or other implant.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:
1. A drill bit, comprising:
a body;
a helical flute extending along a length of the body to a tip;
a first land area extending along the length of the body and forming the largest diameter of the body; and
a second land area extending adjacent the first land area and the tip, where upon rotation of the drill bit in a single direction the second land area is configured to direct created debris toward the first land area while the first land area is configured to compress the debris laterally outward into a side wall of a drill hole, wherein the helical flute rotates in the opposite direction and directs the debris toward the tip.

2. The drill bit of claim 1, wherein the second land area directs debris toward the tip.

3. The drill bit of claim 1, wherein the first land area forms an outer surface of the body.

4. The drill bit of claim 3, wherein the second land area tapers inwardly from the first land area and controls a flow of the debris toward the first land area.

5. The drill bit of claim 1, wherein the first land area has channels configured to hold debris created by the drill bit.

6. The drill bit of claim 1, wherein the drill bit is an osteotome.

7. The drill bit of claim 6, wherein the drill bit is configured to be used during an osteotomy.

8. The drill bit of claim 1, wherein the first land area is narrower than the second land area.

9. The drill bit of claim 1, wherein the second land area is formed on a side of the first land area opposite the flute.

10. The drill bit of claim 1, wherein the second land area has less area than an area of flute.

11. A method of using a drill bit comprising a body, a helical flute extending along a length of the body to a tip, a first land area extending along the length to the body and forming the largest diameter of the body, and a second land area extending adjacent the first land area and the tip, where upon rotation of the drill bit in a single direction the second land area is configured to direct created debris toward the first land area while the first land area is configured to compress the debris laterally outward into a side wall of a drill hole, the method comprising:
attaching the drill bit to a drill; and
drilling the drill bit into a surface of a material in a single direction to form a hole, wherein the second land area directs created debris toward the first land area while the first land area compresses the debris laterally outward into a side wall of the hole, wherein the helical flute rotates in the opposite direction and directs the debris toward the tip.

12. The method of claim 11, wherein the second land area directs the debris toward the tip.

13. The method of claim 11, wherein the first land area forms an outer surface of the body.

14. The method of claim 13, wherein the second land area tapers inwardly from the first land area and controls a flow of the debris toward the first land area.

15. The method of claim 11, wherein the first land area has channels holding debris created by the drill bit.

16. The method of claim 11, wherein the drill bit is an osteotome.

17. The method of claim 15, wherein the method is an osteotomy.

18. The method of claim 11, wherein the first land area is narrower than the second land area.

19. The method of claim 11, wherein second land area is formed on a side of the first land area opposite the flute.

20. The method of claim 11, wherein the second land area has less area than an area of flute.

* * * * *